(12) United States Patent
Offray et al.

(10) Patent No.: US 6,432,138 B1
(45) Date of Patent: Aug. 13, 2002

(54) CONTROLLED POROSITY 3-D FABRIC BREAST PROSTHESIS

(75) Inventors: Denise Ann Offray, Gillette; Durmus Koch, Demarest; John Mortensen, Little Silver, all of NJ (US)

(73) Assignee: Promatrx, Inc., Chester, NJ (US)

( * ) Notice: Subject to any disclaimer, the term of this patent is extended or adjusted under 35 U.S.C. 154(b) by 0 days.

(21) Appl. No.: 09/521,081

(22) Filed: Mar. 7, 2000

(51) Int. Cl.[7] .................................................. A61F 2/12
(52) U.S. Cl. .......................................................... 623/8
(58) Field of Search ........................................ 623/7, 8

(56) References Cited

U.S. PATENT DOCUMENTS

| | | | |
|---|---|---|---|
| 3,858,248 A | | 1/1975 | Crowe ............................... 3/36 |
| 4,507,810 A | | 4/1985 | Bartholdson ...................... 3/36 |
| 4,573,999 A | | 3/1986 | Netto .............................. 623/7 |
| 4,936,858 A | | 6/1990 | O'Keeffe ......................... 623/8 |
| 5,011,494 A | | 4/1991 | von Recum ..................... 623/8 |
| 5,092,348 A | | 3/1992 | Dubrul ........................ 128/899 |
| 5,133,752 A | | 7/1992 | Mandelkern .................... 623/7 |
| 5,207,709 A | * | 5/1993 | Picha ....................... 623/11.11 |
| 5,282,856 A | * | 2/1994 | Ledergerber .................... 623/8 |
| 5,358,521 A | | 10/1994 | Shane ............................ 623/8 |
| 5,458,635 A | | 10/1995 | Berman .......................... 623/8 |
| 5,486,593 A | * | 1/1996 | Tang et al. .................. 528/370 |
| 5,496,376 A | | 3/1996 | Falotico ....................... 252/174 |
| 5,545,217 A | * | 8/1996 | Offray et al. ................... 623/8 |
| 5,653,755 A | * | 8/1997 | Ledergerber .................... 623/8 |
| 5,681,572 A | * | 10/1997 | Seare, Jr. ..................... 424/400 |
| 6,187,043 B1 | * | 2/2001 | Ledergerber .................... 623/8 |

FOREIGN PATENT DOCUMENTS

EP  744 162 A2  11/1996

OTHER PUBLICATIONS

Peptide Growth Factors & Myofibroblasts in Capsule Around Human Breast Implants; Clas Lossing & Hans-Arne Hansson from Plastic Resonstructive Surgery, Jun. 1993 pp. 1277-1285.

Smooth vs. Rough: An 8-Year Survey of Mammary Prostheses by Marshall A. Shapiro from Plastic and Reconstructive Surgery—Sep. 1989 pp. 449-457.

* cited by examiner

Primary Examiner—David H. Willse
Assistant Examiner—Suzette J. Jackson
(74) Attorney, Agent, or Firm—Barry G. Magidoff; Paul J. Sutton

(57) ABSTRACT

A biocompatable nonbiodegradable breast prosthesis comprises a generally conical shell filled with a resilient mass comprised of a multiplicity of layers of resiliently compressible fabric. The shell fabric provides a pore size in the range of from about 2 to 15 microns, 5 microns being preferred.

The filler fabric layers define a void content from 70 to 90% or more and are resilient when subjected to compressive forces in both wet and dry conditions. The layers preferably are a honeycomb weave and are formed of monofilament yarns.

7 Claims, 2 Drawing Sheets

CONTROLLED POROSITY 3-D FABRIC BREAST PROSTHESIS

BACKGROUND OF THE INVENTION

The present invention is directed to a breast prosthesis and more particularly, an implantable prosthesis to be used following removal of diseased body tissue. Still more particularly the invention is directed to a breast prosthesis which is shape retaining and provides, following implant, a tactile sensation virtually indistinguishable from a normal breast.

The invention is further directed to a surgically implanted breast prosthesis comprised entirely of biocompatible non-biodegradable materials. A characterizing feature of the invention resides in the provision of an implant which is resistant to conversion into a hard, relatively non-deformable scar tissue mass such as is characterized by breast implants heretofore known.

PRIOR ART

Reference is made to U.S. Pat. No. 5,545,217, owned by the assignee of the instant application. The noted patent discusses, in detail, prior art attempts to create an implantable breast prosthesis which is comfortable and provides close simulation of a normal breast.

As noted in said reference, the use of liquid silicone implants is counterindicated due to the health effects said to be encountered in the event of leakage of silicone from the encompassing plastic pouch. Pouches filled with saline are similarly undesirable in that the pouch cannot be fully filled without danger of rupture, and a partially filled pouch will exhibit fold lines.

In the above-referenced U.S. patent, there is disclosed an improved implant formed of bio-compatible, non-biodegradable materials. The device comprises a generally conical implant providing a controlled porosity interior filling enabling the in-growth of new blood vessels and tissue throughout the structure of the device. Since the prosthesis ultimately will become infused with blood vessels and tissue of the patient, the body temperature of the breast will be the same as the remainder of the body, in contrast to liquid filled prosthesis which vary from body temperature when subjected to cool or hot environments.

The patent literature is replete with attempts to provide a breast prosthesis implant, which will, over a protracted period of time, remain comfortable to the patient and provide the characteristics of a normal breast.

In addition to the references cited in the '217 Patent, the following references have been located in the course of searches and investigations.

U.S. Pat. No. 3,858,248 discloses an insert for a brassiere formed of a pattern of stitches with a mass of tangled threads in the hollow interior.

U.S. Pat. No. 4,507,810 discloses an implant which has an outer bio-compatible impervious skin and is filled with cells of various sizes, the cells having passages held in fixed position within the casing. The casing is fluid-filled.

U.S. Pat. No. 4,573,999 relates to an elastomeric, fluid-filled prosthesis used as a breast implant, the device having concentric wave-like ripples formed about the conic surface. The peaks of the waves are said to flatten as a result of fibrous in-growth.

U.S. Pat. No. 4,936,858 teaches a net-like fabric material used to surround a sac-type, fluid-filled implant. The fabric provides an anchor for tissue in-growth and is inextensible in one direction, so that the breast does not adopt a spherical configuration following fibrous ingrowth.

U.S. Pat. No. 5,011,494 relates to a soft tissue implant having superior connection properties to surrounding tissue with reduced likelihood of inflammation at the implant site. The material includes openings of a critical size and notes that the structure can be a weave or fused-together elements or a waffle pattern of projections. A preferred method of forming the net material comprises the use of a photo-resist process to define a pattern and casting a polymer onto the pattern.

U.S. Pat. No. 5,092,348 is directed to a tissue expander for creating a fibrous pocket for receiving a subsequently injected implant of a permanent prosthesis. The expander has a textured external surface that is said to optimize the pocket.

U.S. Pat. No. 5,133,752 relates to a non-implant, launderable prosthesis comprising a series of soft porous pads formed of a material such as high-loft bonded polyester fiber. The pads are joined by a basting stitch or the like and allow independent relative movement of the pads.

U.S. Pat. No. 5,358,521 relates to an implantable prosthesis being a sac-within-a-sac of multilayer construction. Lubricants are inserted between the layers of the sacs to reduce the chance that the rubbing of one layer against another could cause wear or rupture. The layers are comprised of impervious silicone elastomer.

U.S. Pat. No. 5,458,635 is directed to an external prosthesis for insertion into a bra and is adaptable by the user to different sizes by addition or subtraction of a number of nesting layers.

U.S. Pat. No. 5,496,376 is directed to an implantable fluid-filled prosthesis having internal baffles to reduce "wave motion".

European reference EP0744162A2 is directed to a surgical implant wherein an array of fibers are positioned on a matrix by embroidery.

GENERAL DISCUSSION

Many attempts have been made to provide a breast prosthesis implant which is bio compatible, comfortable to the patient, and which provides the appearance and tactile sensation of a natural breast. In the 1950s, injections of liquid paraffin and silicone were employed. These materials led to the formation of granulomas and ended in the migration of material to unpredictable parts of the body, as well as skin erosions.

The use of pre-shaped implants of poly vinyl alchohol-formaldihide (Ivalon) sponges, at times coated with polyethylene or polyurethane were likewise attempted. These devices were accompanied by numerous problems including excessive fiber ingrowth, fluid accumulation and deformation, as well as a high infection rate. (Polyetheron) sponges were employed in the 1960s but excessive capsular strictures of this material led to deformity and shrinkage with time.

Silicone gel implants employed in the 1960s comprised a smooth silicone elastic shell surrounding a silicone gel filler. To avoid implant migration, dacron patches were affixed to the back to affix the implant to the chest wall. This product resulted in a high rate of capsular stricture occurrence as well as implant rupture. Smooth walled gel implants placed underneath the breast gland suffered from a significant rate of such strictures as well as implant rupture.

To overcome the stricture problem manufacturers employed texturing of the implant surfaces with the goal of obtaining random orientation of the collagen fiber bundles developed over a period of time. Subsequent devices employing porous shaped implants comprised of biocompatible non-biodegradable polymers have been attempted (e.g., U.S. Pat. No. 5,545,217). Such devices have, universally suffered from defect of the formation of a breast which progressively increases in rigidity with the passage of time. In addition to not providing the tactile sensation of a natural breast, the implant became progressively more uncomfortable to the patient. We have attributed this defect to the uncontrolled filling of the interior of the prosthesis resulting in a progressively increasing tissue content. Similarly, the external shell of the prosthesis had previously been created to be as porous as possible with the thought that high porosity would accelerate tissue ingrowth in the interior of the prosthesis as well as providing a softer more supple exterior.

In contradistinction to the prior art shaped polymer inserts, we have discovered that by providing a prosthesis the conic exterior of which is formed of a material having a critical pore size and the interior of which is filled with a high porosity highly resilient structure, that the implanted breast exhibits characteristics which are stable over time and which closely conforms to the appearance and "feel" of a natural breast.

SUMMARY OF THE INVENTION

The present invention may be summarized as directed to an implantable breast prosthesis of generally conical or frustoconical configuration. The prosthesis is comprised of biocompatible nonbiodegradable materials and includes a fabric shell encasing a porous low density highly resilient mass.

A characterizing feature of the invention resides in the discovery that if the yarns of the conical exterior fabric of the device are woven to provide a pore size from 2 to 15 microns, optimally 5 microns, that a controlled fibroblast orientation will result, leading to the deposition of collagen fibers and other tissues in a predictable organization leaving a sheath or capsulation configuration which is restricted largely to the surface of the sheath.

The sheath remains pliant after tissue ingrowth as opposed to devices heretofore known which result in uncontrolled tissue ingrowth and hardened scar tissue formation both on the sheath and interiorly of the prosthesis.

The interior of the prosthesis of the invention within the sheath is formed of a multiplicity of layers of a fabric which is highly resilient as respects forces exerted perpendicular to the plane of the fabric. The interior fabric, which is hereinafter referred to as "3-D fabric" as hereinafter defined, is formed of highly resilient yarns, preferably monofiliment. The 3-D fabrics are extremely porous such that the interior of the conical prosthesis is at least 60% void and preferably 80% or more void. A stack of the 3-D fabric layers, separated or integrated is readily compressible preferably by a factor of at least about 70% without permanent distortion, the stack returning to its original unstressed condition upon release of compressive forces. The preferred fabric presents a "waffle" like surface whereby lateral shifting of members of the stack is prevented by contact with the shell and by the slight interesting or friction between contacting rugous surfaces.

We have discovered that an implant as described will, after maturation, provide a structure in which the interior of the shell is comprised of a high percentage of liquid, i.e., body plasma with reduced amounts of cell or tissue content as contrasted with implants heretofore known, i.e., that the pore size of the exterior fabric controls the proportion of tissue to fluid within the implant.

The implanted prosthesis after maturation within the patient is shape retaining, essentially the same weight as the natural breast tissues replaced by the implant, and provides the "feel" of a natural breast.

DEFINITIONS

As employed herein, the term 3-D fabric is intended to mean knitted or woven or otherwise constructed fabric, preferably a honeycomb weave which, wet or dry is characterized in its having a high degree of compressibility relative to a force applied perpendicular to the plane of the fabric. In particular, the 3-D fabric should be compressible by a factor of at least 60% and optimally 80% responsive to an applied force of 4 psi and exhibit no significant distortion, i.e., return to its original thickness when the force is removed under either wet or dry conditions.

The 3-D fabric should have a void content of at least 70% and preferably 80% or more.

By way of specific example, and without limitation and in compliance with the "best mode" requirement of the law, a preferred 3-D fabric is comprised of a honeycomb weave pattern having 255 ends per inch by 255 picks per inch. The yarn is a 27 denier monofiliment polyester. The weave pattern is a honeycomb with a 34-end repeat. Loom tension is adjusted to form a fabric of about 0.14 cm thickness A stack of 22 layers of the described honeycomb fabric will exhibit a thickness of approximately 3 centimeters. Applied pressure of 4 psi will reduce the stack thickness to approximately 0.6 centimeters. Upon removal of the weight, the stack will return to its initial unstressed condition with no measurable change from the original unstressed condition.

By way of example there is shown in FIG. 3 a suitable honeycomb weave pattern. It should be understood that this pattern is shown by way of illustration and other weave patterns as well as knit patterns which correspond to the functional specifications noted above (ready compressibility with full return and 60% or greater void factor) may be suitably employed. Use of monofilament yarns is indicated to achieve the desired resilience. The described honeycomb fabric weighs 0.00146 ounces per square inch.

A preferred cover or shell fabric providing the desired 2 to 15 (5 preferred) micron pore structure comprises a fabric having 312 warp ends per inch by 256 picks per inch. The fabric thickness is 0.003 inches and it weighs 0.00132 ounces per square inch. The yarn employed is a 22.5 denier polyester monofilament. A preferred fabric employs a 7/1 left hand twill with 8 end repeat. The described yarn is woven to fabric to provide a pore size of approximately 5 microns on average. It will be appreciated that aside from the critical range of the pore size, no limitations are to be implied relative to the cover fabric (other than the materials being biocompatible and nonbiodegradable.)

DETAILED DESCRIPTION OF THE DRAWINGS

Figure 1:
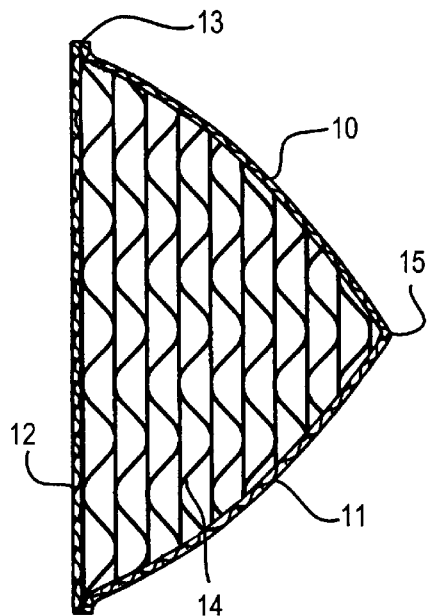
FIG. 1 is a schematic cross section through an implant in accordance with the invention, the fabric components of which are enlarged for purposes of facilitating an understanding of the structure.

FIG. 1 comprises a schematic drawing of a prosthesis in accordance with the invention. The prosthesis is conical in shape including a conical or frustoconical shell fabric 10, including a conical front face 11 and a rear surface 12. The fabric of the shell, as previously described, is formed of a biocompatible non-biodegradable material such as polyethylene terephthalate. As previously noted, the fabric of shell 10 is woven to a critical pore size of about 2 to 15 microns, 5 microns being preferred.

Figure 4:
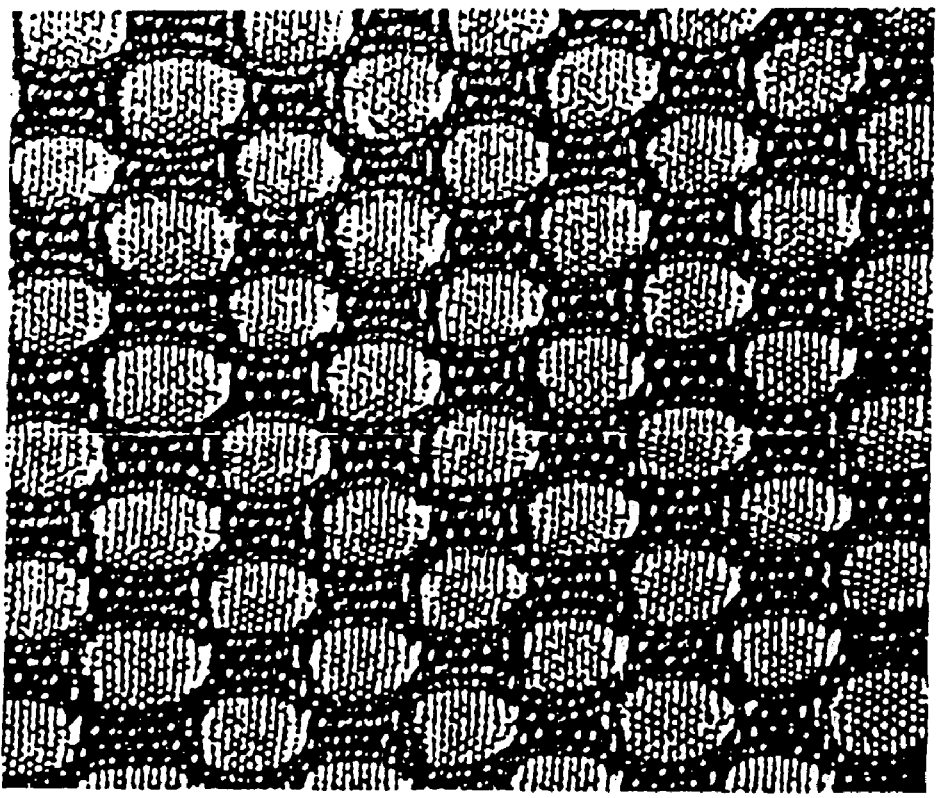
FIG. 4 is a photograph of a representative honeycomb fabric.
Figure 4:
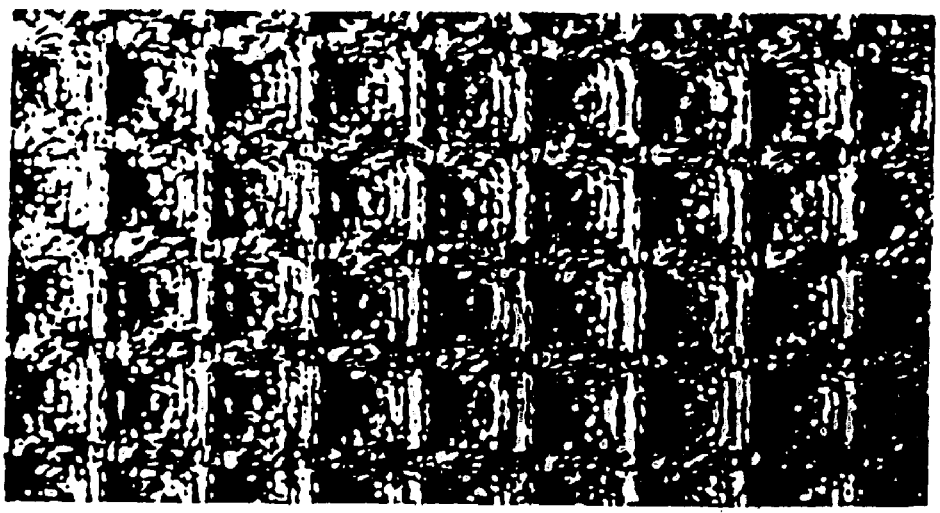

The generally circular contact areas between the elements 11 and 12 are connected preferably by an ultrasonic seal 13. Encased within the shell 10 are a multiplicity of layers of "3-D" fabric 14. An enlarged photograph—plan view of a representative honeycomb fabric is shown in FIG. 4. A representative prosthesis may include a base diameter of 9 centimeters and a height of 5 centimeters. As will be apparent, the transverse extent of the layers 14 diminishes as the layers approach the apex 15 of the cone. In order to obtain a height of approximately 5 centimeters approximately 40 to 50 layers of "3-D" material will be required.

Figure 2:
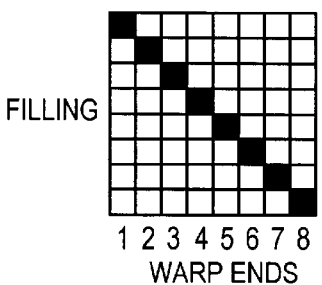
FIG. 2 is a weave pattern of a preferred shell material.

In FIG. 2 there is shown a weave diagram for formation of the shell material 10, the illustrative weave being a 7-1 left hand twill.

Figure 3:
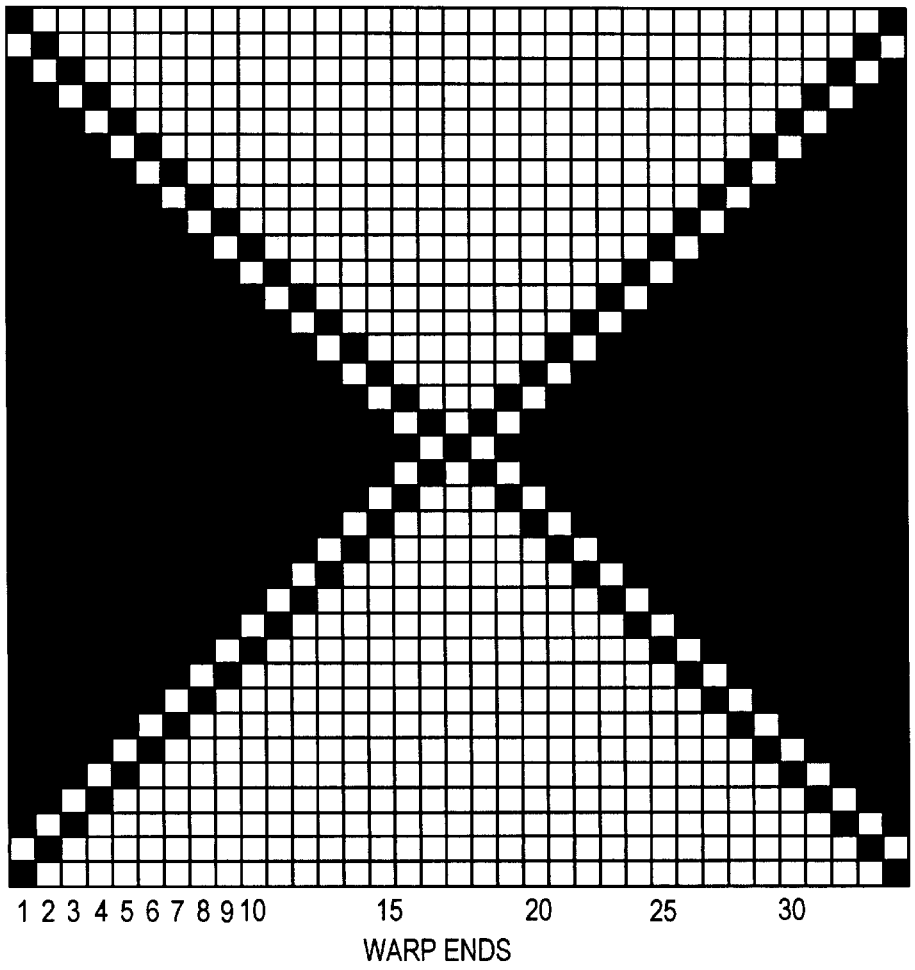
FIG. 3 is a weave pattern of a preferred honeycomb stuffer fabric.

FIG. 3 discloses the interlacings for fabric of a representative example of the desired honeycomb weave "3-D" fabric.

The illustrated prosthesis evinces a void content within the shell of approximately 80%. A pressure exerted against the apex in the direction of the axis of the cone of about 4 psi will reduce the height of the cone to 1 centimeter and upon release the cone will return resiliently to its initial shape with no indication of permanent deformation. This is true under both wet and dry conditions. Obviously, variations in size and to a degree, configuration of the prosthesis will be made in accordance with the requirements of the patient.

The prosthesis will return to its original condition not only against forces exerted in the direction of the axis of the prosthesis but also as respects forces exerted laterally. This shape retaining characteristic is a function of a constraint exerted by shell fabric and also by the fact the honeycomb weave layers tend to internest slightly providing a locking action against relative lateral shifting movements between adjacent layers.

There is shown and described in accordance with the invention a breast prosthesis which, following implant and tissue and fluid influx (maturation) will evince the characteristics of a normal breast. The rigid scar tissue formation accompanying implants herefor known is eliminated with the device of the invention.

It is believed that the success of the implant is derived from the use of a shell of critical pore size which governs the percentage of the interior of the prosthesis which is occupied by tissue on the one hand and by fluids on the other hand. The utilization of a highly porous external shell in prior known devices results in an unacceptably high proportion of tissue in growth and a concomitant unnatural rigidity of the breast. The device of the present invention is effective to control the proportion of liquid and solid in the interior of the prosthesis as well as the characteristics of the lattice work of tissue which appends to the shell itself.

As will be apparent to those skilled in the art and familiarized with the instant disclosure, variations in the configuration and structure of the shell fabric and honeycomb fabric may be made without departing from the spirit of the invention. Particularly, a shell fabric or structure incorporating the critical pore size may be made by methods other than weaving. Similarly, it is conceivable that a filler evincing the necessary resilience and porosity characteristics may be fabricated other than by the use of a woven technique. Accordingly, the invention is to be broadly construed within the scope of the appended claims.

What is claimed is:

1. A biocompatible breast prosthesis implant comprising a fabric shell in the general configuration of a cone and having a base and an apex, a plurality of fabric layers in mutually engaging stacked array within said shell, the perimeters of said layers being disposed proximate interior surfaces of said shell, the transverse dimension of said layers becoming progressively smaller in the direction of said apex, said layers being comprised of monofilament yarns formed into a resilient 3-D fabric and said shell being porous, the pore size of said shell being in the range of, about 2 to 15 microns.

2. The implant of claim 1 wherein the void volume within said shell is from about 70 to 90% of the total enclosed volume of said shell.

3. An implant in accordance with claim 2 wherein said implant may be compressed to a third or more of its initial unstressed volume and will return to its initial configuration responsive to removal of said stress under wet and dry conditions.

4. A bio compatible non-biodegradable breast prosthesis comprising a generally conical shell, a resilient filler within said shell, said shell comprising a pervious fabric having pore size of from about 2 to 15 microns, said filler comprising a plurality of stacked mutually engaging layers of 3-D fabric, said 3-D fabric comprising a monofilament, said filler providing a void content of at least about 80%.

5. A prosthesis in accordance with claim 4 wherein said stacked layers of 3-D fabric are in the general configuration of a cone, said stack characterized in that the same will return to its unstressed shape following application and release of compressive forces which reduce the height of said cone to one eighth of its unstressed height under wet or dry conditions.

6. A prosthesis in accordance with claim 4 wherein the engaging surfaces of adjacent said layers are partially internested whereby relative lateral movement of adjacent layers is impeded.

7. A bio compatible non-biodegradable breast prosthesis comprising a generally conical shell, a resilient filler within said shell, said shell comprising a pervious fabric having a pore size of about 5 microns, said filler comprising a plurality of stacked 3-D fabric layers, said stacked layers including edge portions engaging the interior of said shell, said 3-D fabric comprising a monofilament in a honeycomb weave, said filler providing a void content of at least about 80%.

* * * * *